United States Patent
Wu et al.

(10) Patent No.: US 11,554,173 B2
(45) Date of Patent: Jan. 17, 2023

(54) METHODS OF TRANSFECTION FOR LARGE CARGO USING POLY(BETA-AMINO ESTERS)

(71) Applicant: NanoCav, LLC, Culver City, CA (US)

(72) Inventors: Ting-Hsiang Sherry Wu, Culver City, CA (US); Wade Nichols Richardson, Los Angeles, CA (US)

(73) Assignee: NANOCAV, LLC, Culver City, CA (US)

( * ) Notice: Subject to any disclaimer, the term of this patent is extended or adjusted under 35 U.S.C. 154(b) by 842 days.

(21) Appl. No.: 16/506,478

(22) Filed: Jul. 9, 2019

(65) Prior Publication Data

US 2020/0009259 A1 Jan. 9, 2020

Related U.S. Application Data

(60) Provisional application No. 62/695,457, filed on Jul. 9, 2018.

(51) Int. Cl.
| | |
|---|---|
| *C12N 9/22* | (2006.01) |
| *C12N 15/90* | (2006.01) |
| *C12N 15/113* | (2010.01) |
| *C12N 15/11* | (2006.01) |
| *C12N 15/10* | (2006.01) |
| *A61K 47/58* | (2017.01) |
| *A61K 35/00* | (2006.01) |
| *A61K 39/235* | (2006.01) |
| *C12N 7/00* | (2006.01) |

(52) U.S. Cl.
CPC .............. *A61K 47/58* (2017.08); *A61K 35/00* (2013.01); *A61K 39/235* (2013.01); *C12N 7/00* (2013.01); *C12N 2750/14134* (2013.01); *C12N 2750/14171* (2013.01)

(58) Field of Classification Search
CPC .... C12N 9/22; C12N 2310/20; C12N 15/113; C12N 15/63; C12Q 1/6816
See application file for complete search history.

(56) References Cited

U.S. PATENT DOCUMENTS

| 8,287,849 B2 | 10/2012 | Langer et al. |
| 2018/0112038 A1 | 4/2018 | Green et al. |

FOREIGN PATENT DOCUMENTS

| WO | 2016019126 A1 | 2/2016 |
| WO | WO2016019126 | * 2/2016 |

OTHER PUBLICATIONS

International Search Report from PCT Application No. PCT/US2019/041058 dated Sep. 25, 2019.
Written Opinion from PCT Application No. PCT/US2019/041058 dated Sep. 25, 2019.
Mastorakos, P., et al., "Highly compacted biodegradable DNA nanoparticles capable of overcoming the mucus barrier for inhaled lung gene therapy," PNAS, 112(28): 8720-8725 (2015).
Li, C., et al., "(3-Aminopropyl)-4-methylpiperazine End-capped Poly(1,4-butanediol diacrylate-co-4-amino-1-butanol)-based Multilayer Films for Gene Delivery," ACS Applied Materials and Interfaces, 5(13): 1-17 (2013).
Li, Y., et al., "In situ pneumococcal vaccine production and delivery through a hybrid biological-biomaterial vector," Science Advances, 2(7): 1-9 (2016).
Jones, C.H., et al., "Hybrid biosynthetic gene therapy vector development and dual engineering capacity," PNAS, 111(34): 12360-12365 (2014).
Buo, A.M., et al., "A cost-effective method to enhance adenoviral transduction of primary murine osteoblasts and bone marrow stromal cells," Bone Research, 4: 1-10 (2016).
Dodds, E., et al., "Cationic Lipids and Polymers Are Able to Enhance Adenoviral Infection of Cultured Mouse Myotubes," Journal of Neurochemistry, 72(5): 2105-2112 (1999).
Arcasoy, SM., et al., "Polycations increase the efficiency of adenovirus-mediated gene transfer to epithelial and endothelial cells in vitro," Gene Therapy, 4: 32-38 (1997).
Zhao, C., et al., "Adenovirus-Mediated Gene Transfer in Mesenchymal Stem Cells Can Be Significantly Enhanced by the Cationic Polymer Polybrene," PLOS One, 9(3): 1-8 (2014).
Schaefer, A. M., et al., "Prevalence of Mitochondrial DNA Disease in Adults," Ann Neurol, 63: 35-39 (2008).
Sunshine, J. C., et al., "Uptake and transfection with polymeric nanoparticles are dependent on polymer end-group structure, but largely independent of nanoparticle physical and chemical properties," Mol Pharm., 9(11): 3375-3383 (2012).
Bhise, N.S., et al., "Evaluating the potential of poly(beta-amino ester) nanoparticles for reprogramming human fibroblasts to become induced pluripotent stem cells," International Journal of Nanomedicine, 8: 4641-4658 (2013).
Mangraviti, A., et al., "Polymeric Nanoparticles for Nonviral Gene Therapy Extend Brain Tumor Survival in Vivo," AcsNano, 9(2): 1236-1249 (2015).

* cited by examiner

*Primary Examiner* — Barry A Chestnut
(74) *Attorney, Agent, or Firm* — Harness Dickey & Pierce P.L.C.

(57) ABSTRACT

Methods are provided for transfecting cells with large cargo using a poly(beta-amino ester) (PBAE) molecule, and achieving high efficiency and viability. A method is provided of transfecting cells with a cargo, by forming a complex of the cargo with a (PBAE) molecule, mixing the complex with a first buffer and contacting the complex with the cells, wherein the cargo has a dimension of at least 0.1 μm. The PBAE molecule may be formed by reacting an amine with a di(acrylate ester). In some aspects, the PBAE molecule is poly(1,4-butanediol diacrylate-co-4-amino-1-butanol). In some aspects, the PBAE molecule is capped with 1-(3-aminopropyl)-4-methylpiperazine.

43 Claims, 14 Drawing Sheets

METHODS OF TRANSFECTION FOR LARGE CARGO USING POLY(BETA-AMINO ESTERS)

CROSS REFERENCE TO RELATED APPLICATIONS

This application claims priority under 35 U.S.C. § 119(e) from U.S. Provisional Patent Application Ser. No. 62/695,457, filed Jul. 9, 2018, the entire contents of which are hereby incorporated by reference

FIELD OF THE INVENTION

The field of the invention is transfection methods, and in particular, using poly(beta-amino esters) (PBAEs) to transfect large cargo such as mitochondria into recipient cells.

BACKGROUND OF THE INVENTION

The background description includes information that may be useful in understanding the methods and techniques presented herein. It is not an admission that any of the information provided herein is prior art or relevant to the subject matter presented herein, or that any publication specifically or implicitly referenced is prior art.

Various transfection techniques for introducing nucleic acids into cells to produce genetically modified cells are known in the art. These techniques include optoperforation, microinjection, electroporation, viral transduction, and lipid mediated methods (e.g., using liposome-DNA complexes), as well as poly (beta) amino acids for DNA and RNA transfection. Some of these methods are prohibitive due to high cost or poor efficacy. Other methods, e.g., lipid based methods, do not work well with certain cell types of clinical interest, e.g., natural killer (NK) cells. While commercial products exist, these products are not optimal for transfecting all cell types or all types of cargo, and often lead to poor yield and/or issues with cell viability. Typical electroporation rates may yield 2-5% DNA transfection efficiencies with about 10-20% cell viability.

Methods for transferring mitochondrial DNA (mtDNA), which may be packaged inside mitochondria, into cells are limited by a variety of factors, including low yield/throughput, limited cell type availability, selection difficulties, contamination from other cellular components, as well as unreliability and/or inconsistencies in transfer of mtDNA into recipient cells. In some cases, such methods may rely on spontaneous biological processes, which are associated with low yield.

Mitochondria has been implicated in a variety of diseases, including mitochondrial disorders, cardiac dysfunction, heart failure, autism, diabetes mellitus, and deafness. These diseases may arise in part because mtDNA lack proofreading capability during mtDNA replication, which may lead to a high rate of mutations. Accordingly, as an individual ages, mtDNA mutations may accumulate and clonally expand in various tissues, including but not limited to nerve cells, cardiomyocytes, skeletal muscle cells, colon tissue, etc. Some estimates place the prevalence of mtDNA disease at about 1 in 5,000 individuals (Schaefer et al., Ann Neurol (2008) v 63:35-9).

One approach to treat mitochondrial diseases is to target diseased cells with wild type mtDNA, absent mutations or other known defects. However, methods to transfect large molecules into cells are limited. As traditional transfection techniques often have poor yield, especially as the size of the cargo increases, recent techniques have relied upon mechanical techniques involving applied force to improve yields. However, while force-dependent techniques may have improved yield, these techniques are necessarily performed ex-vivo. Treatment of a patient would therefore involve extraction of diseases cells from a patient, transfection with corrected mtDNA, and transfer back into the patient.

While poly(beta-amino esters) (PBAEs) have been used for DNA and RNA transfection in vitro as well as in vivo, these studies have been limited to transfection of small molecules such as nucleic acids.

Even though various transfection systems and methods exist for mammalian cells, these techniques typically involve transfer of small molecules such as DNA and RNA. Accordingly, there is still a need to provide improved transfection systems and methods for large cargo and/or for techniques that may be applied in vivo.

SUMMARY

The techniques presented herein are directed to transfection of cargo, for example, larger cargo, into cells using PBAEs. A method is provided of transfecting cells with a cargo, comprising forming a complex of the cargo with a poly(beta-amino ester) (PBAE) molecule and contacting the complex with the cells, wherein the cargo has a dimension of at least 0.1 µm. The PBAE molecule may be formed by reacting a primary amine with a di(acrylate ester). In some aspects, the PBAE molecule is poly(1,4-butanediol diacrylate-co-4-amino-1-butanol). In some aspects, the PBAE molecule is an end-capped PBAE molecule formed by reaction the PBAE molecule with a capping amine, for example, 1-(3-aminopropyl)-4-methylpiperazine. In some aspects, the concentration of PBAE molecule may be from about 1.0 to about 20 mg/ml, from about 1.0 to about 10 mg/ml, or from about 1.0 to about 5.0 mg/ml. In other aspects, the cargo is mitochondria, a protein, an exosome, an organelle, or a tumor antigen having at least one dimension that is at least 0.1 µm. In other aspects, the cargo may be bacteria, yeast, viruses (e.g., Adv5, Polio, etc.), etc. having at least one dimension that is at least 0.1 µm.

In some aspects, mitochondria from any origin (e.g., endogenous, genetically engineered, etc.) may be transfected into recipient cells using the methods provided herein. Mitochondria may be isolated from any suitable tissue, including but not limited to liver, kidney, skeletal muscle, neurons, retina, cardiac muscle, etc. Commercially available kits are available for isolating mitochondria from tissue.

Mitochondria may be isolated from any suitable species including but not limited to *Homo sapiens, Bos Taurus, Mus musculus, Xenopus laevis, Plecoglossus altivelis, Pan paniscus, Gorilla gorilla, Lemur catta, Cebus albifrons, Tarsius bancanus, Hylobates lar, Rattus norvegicus, Pogona vitticeps, Bufo marinus*, etc. In some cases, the mitochondria to be transfected may be fully functional/active, in other cases, the mitochondria may be inactive or defective, etc.

Any suitable target comprising a membrane may be transfected with the cargo. In some cases, the transfected target may act as vaccine vehicles for vaccine delivery.

In some aspects, recipient cells may be capable of transferring received mitochondria to other cells. Thus, donor cells may be transfected with mitochondria, may contact a target cell, and may transfer their mitochondria to the target cell.

In other aspects, a method of in vivo transfection is provided. The method includes, forming a complex of a cargo with a PBAE molecule and administering the complex mixed with an isotonic buffer to a patient to treat a disease or disorder, wherein the cargo has a dimension that is at least 0.1 μm. The PBAE molecule may be formed by reacting a primary amine with a di(acrylate ester). In some aspects, the PBAE molecule is poly(1,4-butanediol diacrylate-co-4-amino-1-butanol). In some aspects, the PBAE molecule is an end-capped PBAE molecule formed by reacting the PBAE molecule with a capping amine, for example, 1-(3-aminopropyl)-4-methylpiperazine.

Various objects, features, aspects and advantages of the subject matter described herein will become more apparent from the following detailed description of preferred embodiments, along with the accompanying drawing figures in which like numerals represent like components.

DETAILED DESCRIPTION

Methods are provided for transfection of large cargo (e.g., such as mitochondria, etc.) into cells using PBAEs. Such technique are suitable for in vivo treatment of diseases and disorders.

Previous studies have shown that cells may be transfected with nucleic acids using PBAE, and that resulting nanoparticle complexes of PBAE and nucleic acids are formed having dimensions in the range of 130-220 nm (see, Sunshine et al., Mol. Pharm (2012) 9:3375). PBAEs may act as cargo delivery agents during transfection processes, by condensing plasmid DNA into nanoparticles, promoting cellular uptake and escape from the endosome, and facilitating cargo release, e.g., by polymer degradation, into the cytoplasm.

PBAEs are a class of polymers—poly (beta) amino esters—formed by reacting an amine with a di(acrylate ester). Without intending to be limiting, examples of PBAEs may be found in the literature (e.g., U.S. Pat. No. 8,287,849; U.S. Patent Application No. 2018/0112038; Sunshine et al., Mol. Pharm. (2012) 9:3375; Bhise et al., Intl. Journal of Nanomedicine (2013) 8:4641; and Mangraviti et al., ACSNano (2015) 9:1236). Examples of PBAEs are found in these aforementioned references, and these molecular structures are incorporated by reference herein in their entirety.

Figure 1A:
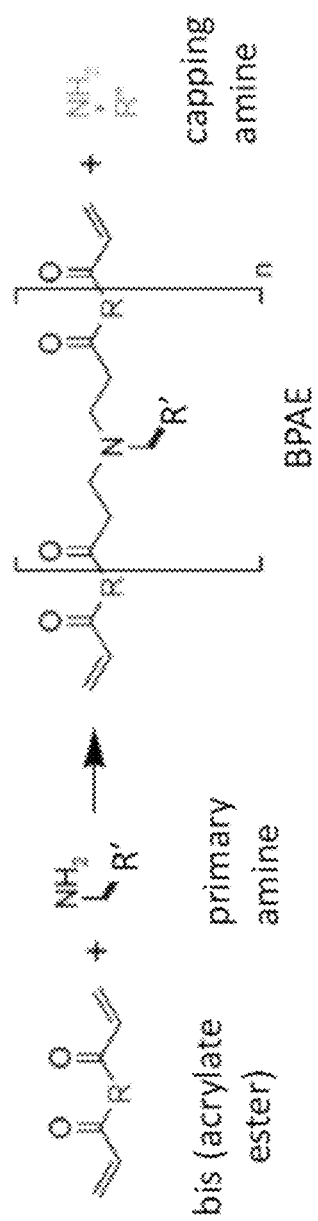
FIGS. 1A-1B show a generalized structure and synthesis of PBAEs, according to some embodiments provided herein.
Figure 1B:
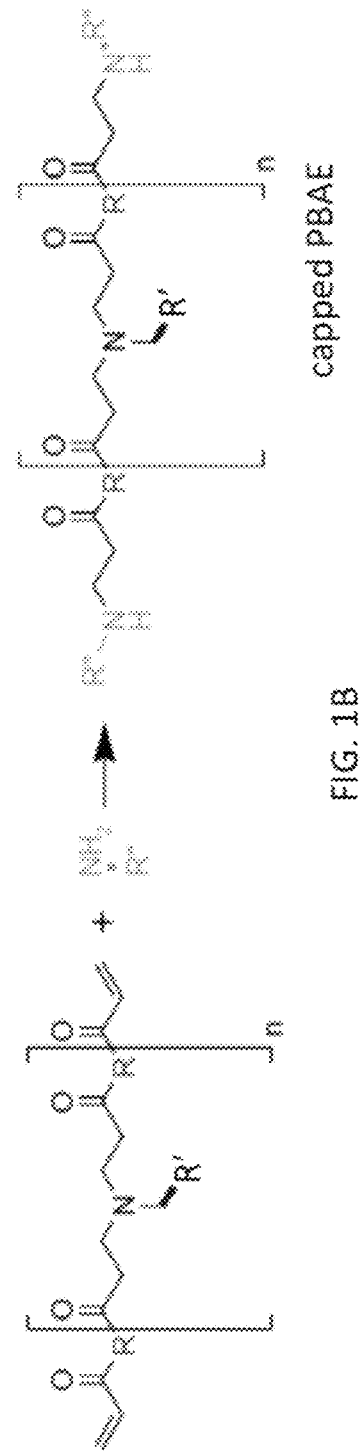

FIGS. 1A and 1B show an example generalized reaction of forming a PBAE (FIG. 1A), followed by a capping reaction with the PBAE (FIG. 1B).

In FIG. 1A, the PBAE molecule is formed by reacting a primary amine with a bis (acrylate ester). Group R may have the form —O-P-O—, wherein O is an oxygen, and group P is a linker or polymer. In some aspects, the P group may be any substituted or unsubstituted, branched, unbranched or cyclic chain of carbon atoms or heteroatoms. In some aspects, group P may refer to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. For example, P may be a $C_1$-$C_{20}$-alkylene, a $C_1$-$C_{15}$-alkylene, a $C_1$-$C_{12}$-alkylene, $C_1$-$C_8$-alkylene, a $C_1$-$C_6$-alkylene or a $C_1$-$C_4$-alkylene. Group P may be optionally unsaturated and/or substituted with one or more alkyl groups. Group P may optionally include one or more oxygen, sulfur or substituted or unsubstituted nitrogen atoms (also referred to as "alkylaminoalkyl"). In some aspects, and as examples, Group P may include one or more substituents selected from the group consisting of hydrogen atoms, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, or ureido groups. In any embodiment, "n" may be an integer from 1 to 10,000, from 1 to 1,000, from 1 to 100, from 1 to 30, from 5 to 20, from 10 to 15, or from 1 to 10. As further examples, in some embodiments, the bis acrylate ester may be 1,4-butanediol diacrylate; 1,5-pentanediol diacrylate; 1,3-propanediol diacrylate; 1,6-hexanediol diacrylate; 1,3-butanediol diacrylate; or 1,4-cyclohexanedimethanol diacrylate.

The primary amine may have any suitable structure provided that a terminal $NH_2$ group is present. For example, in some embodiments, the primary amine may correspond to the formula, $NH_2R'$. In some embodiments, the R' group may be any substituted or unsubstituted, branched, unbranched or cyclic chain of carbon atoms or heteroatoms. In some embodiments, the R' group may be an alkyl group, wherein the alkyl group is a saturated, straight- or branched-chain, substituted or unsubstituted hydrocarbon moiety. For example, R' may be a $C_1$-$C_{20}$-alkyl, a $C_1$-$C_{15}$-alkyl, a $C_1$-$C_{12}$-alkyl, $C_1$-$C_8$-alkyl, a $C_1$-$C_6$-alkyl, a $C_1$-$C_4$-alkyl, or $C_1$-$C_2$-alkyl. The R' group can be optionally unsaturated and/or substituted with one or more alkyl groups. The R' group may optionally include one or more oxygen, sulfur or substituted or unsubstituted nitrogen atoms.

Additionally or alternatively, the R' group may be —$R^aR^b$. In some embodiments, $R^a$ and $R^b$ each independently may be any substituted or unsubstituted, branched, unbranched or cyclic chain of carbon atoms or heteroatoms. In some embodiments, $R^a$ may refer to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. For example, $R^a$ may be a $C_1$-$C_{20}$-alkylene, a $C_1$-$C_{15}$-alkylene, a $C_1$-$C_{12}$-alkylene, $C_1$-$C_8$-alkylene, a $C_1$-$C_6$-alkylene, a $C_1$-$C_4$-alkylene, or a $C_1$-$C_2$-alkylene. In some aspects, $R^b$ may be a hydroxyl group (—OH) or an amino group (—$NH_2$). In particular, $R^b$ may be a hydroxyl group. $R^a$ and $R^b$ each independently may be optionally unsaturated and/or substituted with one or more alkyl groups. $R^a$ and $R^b$ each independently may optionally include one or more oxygen, sulfur or substituted or unsubstituted nitrogen atoms. As further examples, in some embodiments, the primary amine may be 3-amino-1-propanol, 4-amino-1-butanol, 5-amino-1-pentanol, 2-(4-hydroxyphenyl)ethylamine, or 4-amino-N,N-dimethylbutanamide.

In some aspects and as shown in FIG. 1B, PBAE may be capped with another amino group, by reacting PBAE with a capping amine to provide the desired structure of an amine end-capped PBAE molecule The capping amine may correspond to the formula, $NH_2$—R". The R" group may be any substituted or unsubstituted, branched, unbranched or cyclic chain of carbon atoms or heteroatoms. The R" group can be optionally unsaturated and/or substituted with one or more alkyl groups. The R" group may optionally include one or more oxygen, sulfur or substituted or unsubstituted nitrogen atoms. In some embodiments, the R" group may be an alkyl group or a nitrogen-containing alkyl group. The alkyl group may a saturated, straight- or branched-chain, substituted or unsubstituted hydrocarbon moiety. For example, R" may be a $C_1$-$C_{20}$-alkyl, a $C_1$-$C_{15}$-alkyl, a $C_1$-$C_{12}$-alkyl, $C_1$-$C_8$-alkyl, a $C_1$-$C_6$-alkyl, a $C_1$-$C_4$-alkyl, or $C_1$-$C_2$-alkyl. Additionally or alternatively, the R" group may be a nitrogen-containing alkyl group. The term "nitrogen-containing alkyl" refers to an alkyl group herein wherein one or more carbon atoms in the alkyl group is replaced with a nitrogen atom or a nitrogen-containing cyclic hydrocarbon having from 2 to 10 carbon atoms (i.e., a nitrogen-containing cyclic $C_2$-$C_{10}$ hydrocarbon), particularly having from 2 to 5 carbon atoms (i.e., a nitrogen-containing cyclic $C_2$-$C_5$ hydrocarbon), The nitrogen-containing cyclic hydrocarbon may have one or more nitrogen atoms. The nitrogen atom(s) may optionally be substituted with one or more alkyl groups as described herein. In some embodiments, the nitrogen-containing alkyl can have from 1 to 20 carbon atoms (i.e. $C_1$-$C_{20}$ nitrogen-containing alkyl), from 1 to 15 carbon atoms (i.e. $C_1$-$C_{15}$ nitrogen-containing alkyl), from 1 to 10 carbon atoms (i.e. $C_1$-$C_{10}$ nitrogen-containing alkyl), or from 1 to 8 carbon atoms (i.e. $C_1$-$C_8$ nitrogen-containing alkyl). An example of a nitrogen-containing alkyl includes, but is not limited to,

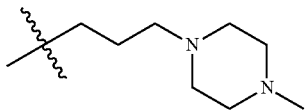 [SMILES: *CCCN1CCN(C)CC1]

Additionally or alternatively, the R" group may be —$R^c R^d$. In some embodiments, $R^c$ and $R^d$ each independently may be any substituted or unsubstituted, branched, unbranched or cyclic chain of carbon atoms or heteroatoms. In some embodiments, $R^c$ may refer to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. For example, $R^c$ may be an alkylene or a nitrogen-containing alkylene. $R^c$ may be a $C_1$-$C_{20}$-alkylene, a $C_1$-$C_{15}$-alkylene, a $C_1$-$C_{12}$-alkylene, $C_1$-$C_8$-alkylene, a $C_1$-$C_6$-alkylene, a $C_1$-$C_4$-alkylene, or a $C_1$-$C_2$-alkylene. The term "nitrogen-containing alkylene" refers to an alkylene group as defined herein wherein one or more carbon atoms in the alkylene group is replaced with a nitrogen atom. The nitrogen atom(s) may optionally be substituted with one or more alkyl groups as described herein. The nitrogen-containing alkylene can have from 1 to 20 carbon atoms (i.e. $C_1$-$C_{20}$ nitrogen-containing alkylene), particularly from 1 to 15 carbon atoms (i.e. $C_1$-$C_{15}$ nitrogen-containing alkylene), particularly from 1 to 10 carbon atoms (i.e. $C_1$-$C_{10}$ nitrogen-containing alkylene), or from 1 to 8 carbon atoms (i.e. $C_1$-$C_8$ nitrogen-containing alkyl). An example of a nitrogen-containing alkylene includes, but is not limited to,

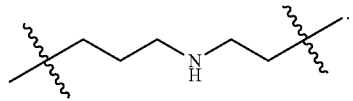 [SMILES: *CCCNCC*]

In some aspects, $R^d$ may be a hydroxyl group (—OH) or an amino group (—$NH_2$). $R^c$ and $R^d$ each independently may be optionally unsaturated and/or substituted with one or more alkyl groups. $R^a$ and $R^b$ each independently may optionally include one or more oxygen, sulfur or substituted or unsubstituted nitrogen atoms. As further examples, in some embodiments, the capping amine may be pentane-1,3-diamine, 2-((3-aminopropyl)amino)ethan-1-ol, 1-(3-aminopropyl)-4-methylpiperazine, 1,3-diaminopropane, or [$NH_2(CH_2CH_2O)_m CH_2CH_2NH_2$], wherein m can be an integer from 3 to 12. In any embodiment, the PBAE molecule may be a pentane-1,3-diamine end-capped PBAE molecule, a 2-((3-aminopropyl)amino)ethan-1-ol end-capped PBAE molecule, a 1-(3-aminopropyl)-4-methylpiperazine end-capped PBAE molecule, a 1,3-diaminopropoane end-capped PBAE molecule, or a [$NH_2(CH_2CH_2O)_m CH_2CH_2NH_2$] end-capped PBAE molecule.

In any embodiment, the PBAE molecule may be selected from the group consisting of poly(1,4-butanediol diacrylate-co-4-amino-1-butanol); poly(1,5-pentanediol diacrylate-co-4-amino-1-butanol); poly(1,4-butanediol diacrylate-co-5-amino-1-pentanol); and poly(1,5-pentanediol diacrylate-co-5-amino-1-pentanol). Any of the PBAE molecules may be end-capped as described above.

Figure 2:
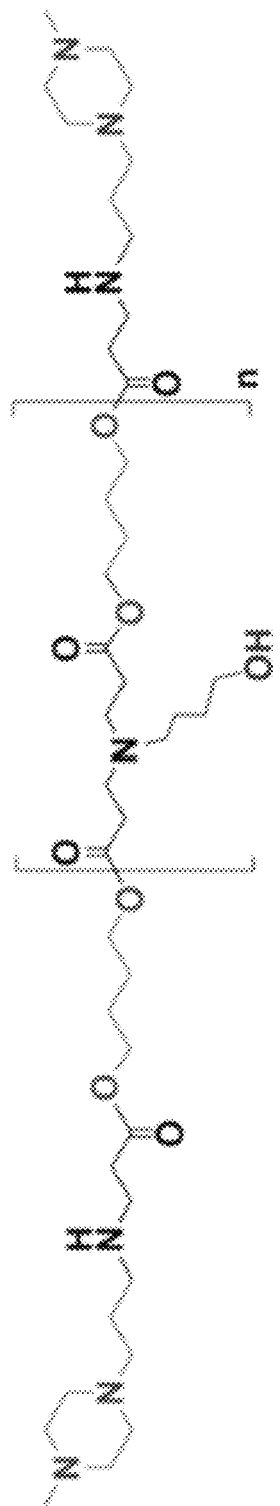
FIG. 2 shows a specific structure of a capped PBAE molecule, according to some embodiments provided herein.
Figure 3A:
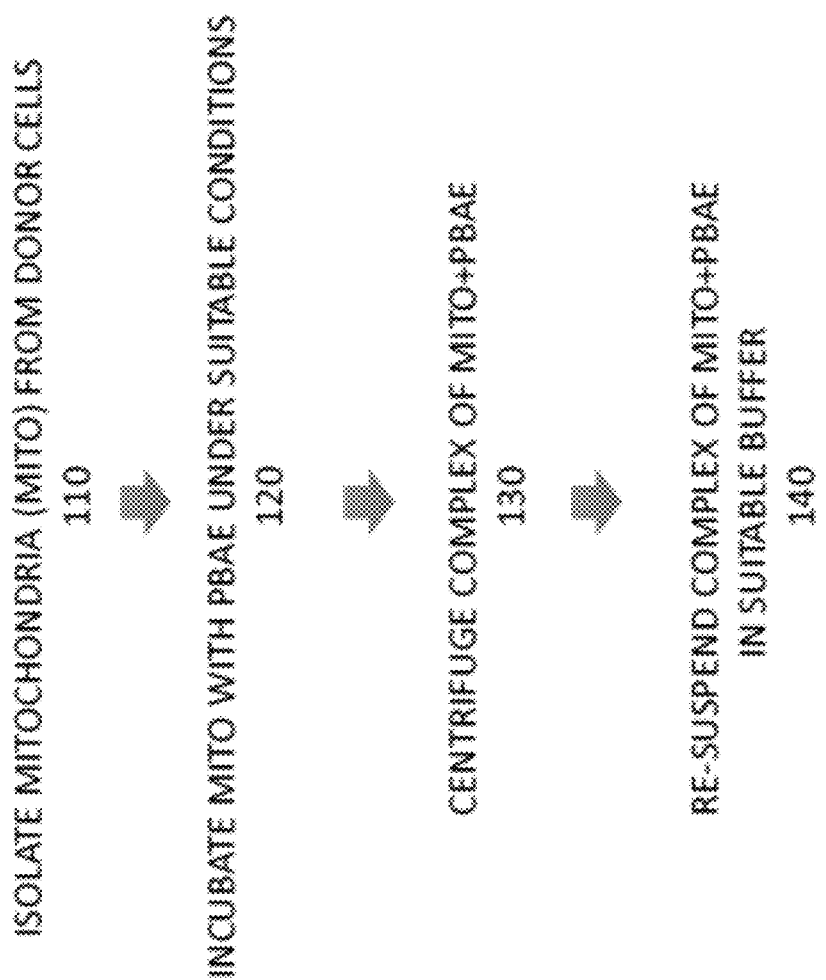
FIGS. 3A-3B show an example process for transfecting cells with mitochondria using PBAE, according to some embodiments provided herein.
Figure 3B:
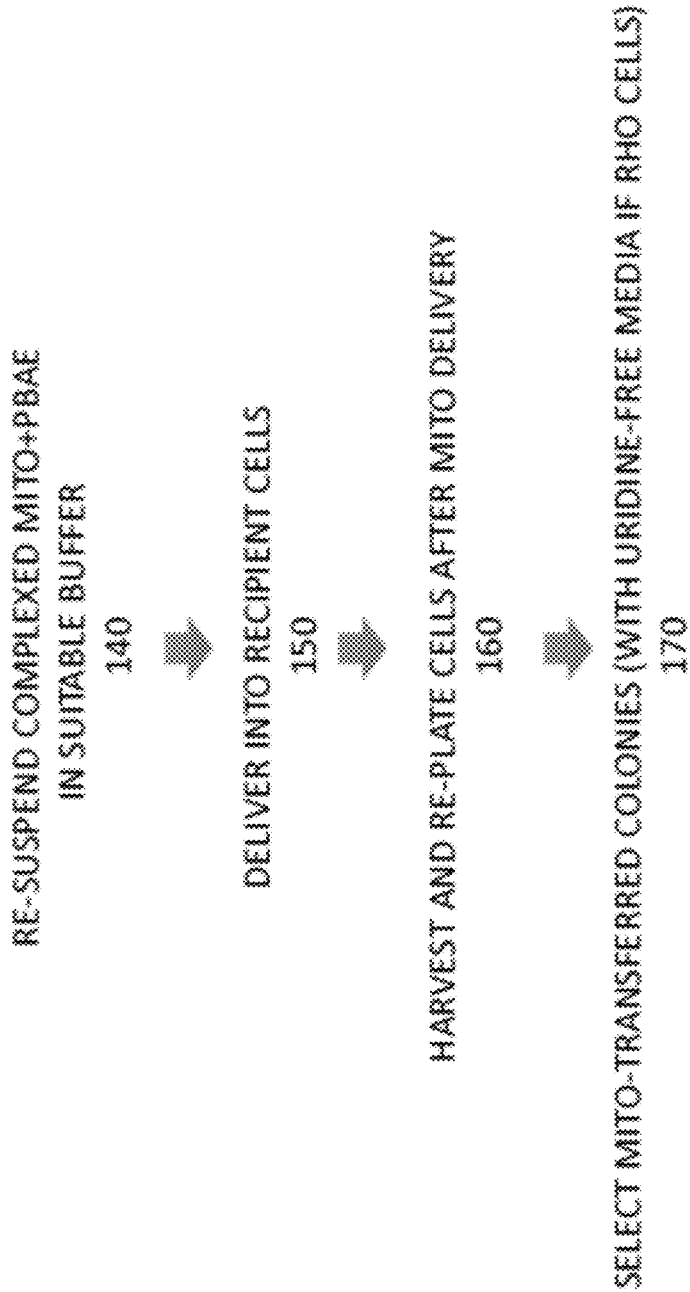
Figure 4:
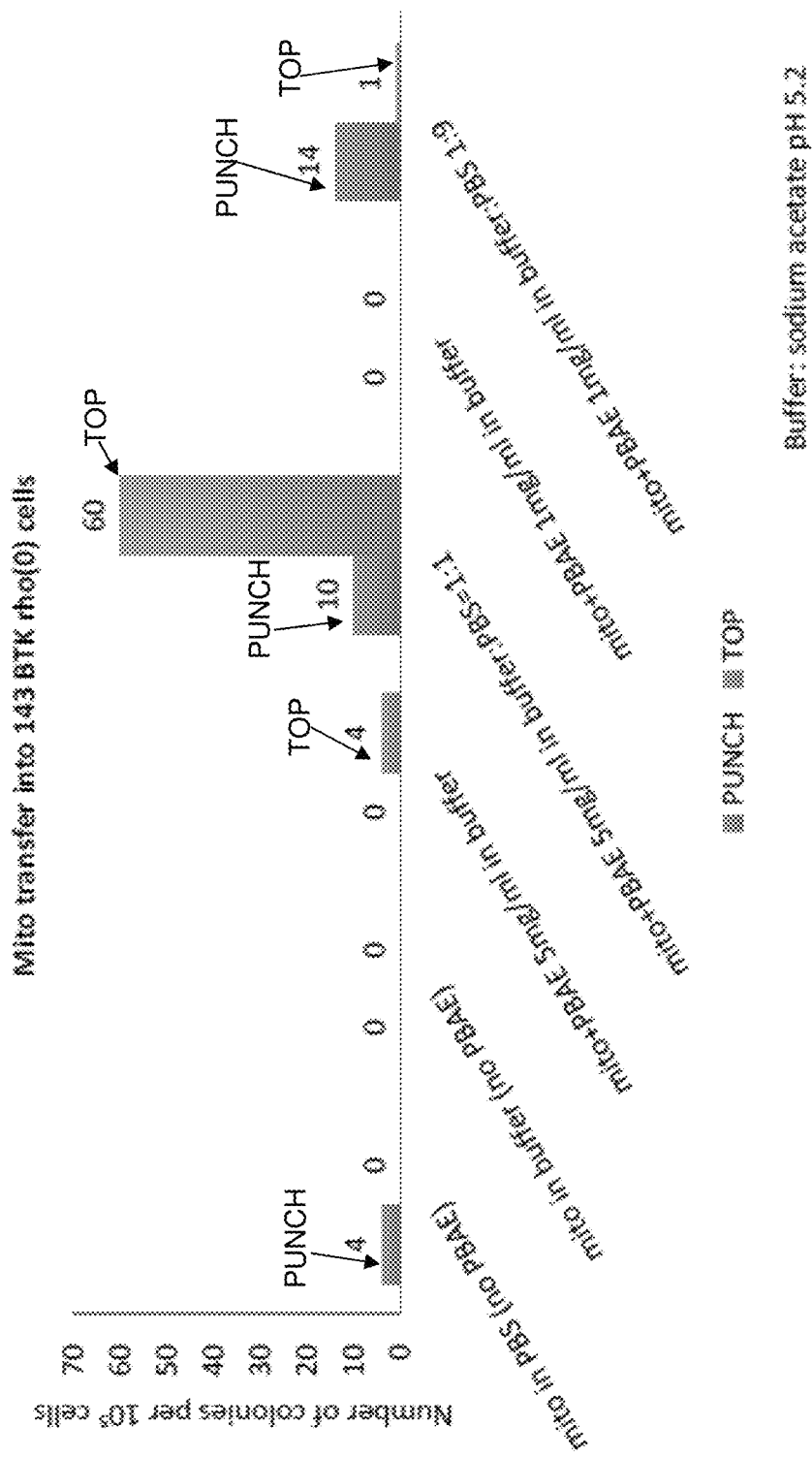
FIG. 4 shows experimental results, based on the process of FIG. 3, according to some embodiments provided herein.

FIG. 2 shows a particular capped PBAE that was used in the process of FIGS. 3A-3B, and also in the experimental results of FIG. 4. This molecule may be synthesized using 1,4-butandiol diacrylate and 4-amino-1-butanol, and capped in a reaction using 1-(3-aminopropyl)-4-methylpiperazine to form 1-(3-aminopropyl)-4-methylpiperazine end-capped poly-(1,4-butanediol diacrylate-co-4-amino-1-butanol). The molecular weight (Mw) of this molecule is can be between 5 kDa and 40 kDa. It is understood by a person of ordinary skill in the art that the molecular can depend on time, temperature and molar ratio of monomer used.

Modifications of PBAEs are also contemplated herein, and may include variations along the backbone (e.g., the R group, the side chain (the R' group), and the end-group (R")) of the capped PBAE molecules. Such variations may include varying the length of the diacrylate backbone, varying the side chain of the amine, and using different functional groups to cap the end of the molecule (see, e.g., Sunshine et al., supra; and Bhise et al., supra). PBAEs degrade rapidly in aqueous solution (e.g., by hydrolysis) to release cargo, such as mitochondria, into the cell.

Characteristics of PBAEs, e.g., the backbone of PBAEs, sidechains of PBAEs, and ends of PBAEs may be modified so as to adjust properties impacting delivery and release of the cargo including hydrophobicity, polymer degradation, optimization of charge, etc. The chemical properties of the PBAE need to allow binding to the cargo, endocytosis and endosomal escape, as well as intracellular cargo release.

For example, it may be desirable to modify the hydrophobicity of the PBAE polymer (to reach an optimal range) in order to improve mitochondrial uptake and transfection efficiency (see, Sunshine et al., supra). In other cases, the buffering capacity of the PBAE polymer, as impacted by the presence of amino groups, may be optimized to improve endosomal escape after cellular uptake. In some embodiments, PBAE polymers may be end-capped with amines or other functional groups to improve buffering capability and uptake. Polymer degradation within the cell environment may also be optimized by inserting hydrolysis sites into the polymer backbone. In still other aspects, the characteristics of PBAE may be varied to optimize the overall charge of the nano- or micro-structures.

The PBAE molecule, which optionally may be capped, may be mixed with the cargo to form a cargo and PBAE complex (cargo+PBAE complex). Examples of suitable cargo include, but are not limited to mitochondria, a protein, an exosome, an organelle, a tumor antigen, bacteria, yeast, a virus (e.g., AdV5, Polio, etc.), and combinations thereof. Once the cargo+PBAE complex is taken up into the cell, the cargo (e.g., mitochondria) may be released into the cell by degradation of the complex, by osmotic swelling, or some other suitable process. In some embodiments, the PBAE polymer may be designed to be sensitive to lysosomal pH to effect degradation of the PBAE polymer once inside the cell.

In other aspects, the PBAE polymer may be designed to be sensitive to the tumor microenvironment, e.g., a tumor sensitive linker that is sensitive to hypoxia, in order to deliver the cargo+PBAE complex to tumor cells. In this embodiment, PBAE may be complexed with a cargo designed to treat a tumor cell, and may also include a targeting molecule (e.g., an antibody or fragment, a protein, etc.) to deliver the complex to the desired tumor cell.

Surprisingly, PBAEs were found to be capable of delivering a large cargo (e.g., mitochondria) into a cell. Mechanical force was not needed for transport to occur. The cargo (e.g., mitochondria) may have at least one dimension, for example, diameter, length, width, of greater than or equal to about 0.1 μm, greater than or equal to about 0.25 μm, greater than or equal to about 0.5 μm, greater than or equal to about 1 μm, greater than or equal to about 2.5 μm, greater than or equal to about 5 μm, greater than or equal to about 7.5 μm, or about 10 μm; or from about 0.1 μm to about 10 μm, about 0.25 μm to about 10 μm, about 0.5 μm to about 10 μm, about 0.5 μm to about 5 μm, or about 0.5 μm to about 2.5 μm. Thus, PBAE is able to deliver large cargo having at least one dimension in the range of 0.1 μm to about 10 μm. In some cases, the cargo, for example, mitochondria, may have a rod-like shape, while in other embodiments, the cargo, for example, mitochondria, may be ovoid, tubular, etc. Complexes of PBAE formed with mitochondria can be significantly larger than nucleic acid (DNA/RNA) complexes formed with PBAE. Accordingly, particles undergoing transfection into recipient cells may range in size from at least about 0.1 μm to 10 μm or more. It was also determined that PBAE was needed for colony formation, as colony formation was not observed without PBAE (assuming no mechanical force) as described herein (see, FIG. 4).

Any suitable recipient cell may be selected for transfection with cargo+PBAE complexes. Recipient cells include, but are not limited to NK cells, EC-7 cells, T cells, mesenchymal cells, immune cells, lymphocytes, dendritic cells (DCs), monocyte-derived dendritic cells (MoDCs), etc. or any other cell in which introduction of mtDNA (packaged within mitochondria) or other large cargo is desired. In some cases, cells which have been transfected with the cargo described herein (e.g., mitochondria) may be transferred back into the individual from which the cargo (e.g., mitochondria) was obtained in order to treat a disease. Examples of diseases include, but are not limited to a mitochondrial disorder, cardiac dysfunction, heart failure, autism, diabetes mellitus, and deafness. In other cases, the cargo+PBAE complex may be injected into the recipient for in vivo therapy. In some aspects, recipient cells may be mammalian cells, human cells, etc. In other cases, the present techniques may be used to transfect bacteria, or any other membrane enclosed vehicle, e.g., wherein the membrane has a negative charge and is able to form an electrostatic complex with the polymer PBAE.

Kits are also provided herein. Kits can include one or more of a PBAE molecule as described herein, the cells as described herein, the cargo described herein, a first buffer as described herein, and an isotonic buffer as described. Additionally or alternatively, reagents for forming the PBAE molecule may also be included in a kit. For example, a primary amine as described herein, a di(acrylate ester) as described herein, a capping amine as described herein, or a combination thereof may be included in a kit.

As shown in FIGS. 3A-3B, a sample experimental protocol is shown. It is understood that many variations are possible herein, and all are contemplated for use. In this case, the cargo is mitochondria, however, it is contemplated herein that a similar procedure may be used for other cargo, for example, a bacteria, a yeast, or a virus.

At step 110, and at time t=0, mitochondria to be delivered into a recipient cell are isolated from a donor cell. Donor cells may include any suitable cell type. For the purposes of this study, DsRed HEK cells were chosen. At step 120, the isolated mitochondria may be incubated with PBAE under suitable conditions. For this study, suitable conditions included a first buffer, such as sodium acetate buffer (sodium acetate (NaOAc) at a pH of about 5.2), and an incubation time of about 5 minutes. Any suitable buffer may be used as an alternative to NaOAc; for example, a mildly acidic buffer such as a citrate buffer.

The pH may also be varied in order to optimize formation of mito+PBAE complexes. The final pH of the solution in which the complexes are formed may be a function of the initial pH, the specific buffer added (e.g., NaOAc, PBS, etc.), and PBAE concentration. The final pH may be a factor in determining whether a given PBAE concentration will be soluble in a given buffer, and therefore, the pH may be adjusted as PBAE solubility may limit formation of mito+PBAE complexes.

After incubation, at step 130, the solution comprising a mito+PBAE complex may be spun down (e.g., in a centrifuge or any other suitable device). In some aspects, a mito+PBAE complex may form nanoparticles or microparticles that are pelleted upon centrifugation. At step 140, the pelleted complex is re-suspended in a buffer suitable for cells, e.g., a buffer having the same or similar osmolarity and ion concentrations—an isotonic buffer—as living cells. Suitable buffers include but are not limited to phosphate buffered saline (PBS) and tris-buffered saline (TBS).

At step 150, the mito-PBAE complexes are delivered into recipient cells. In some cases, the recipient cells include but are not limited to 143BTK rho(0) cells. At step 160, the cells are harvested and re-plated. This may be performed within or up to about 24 hours after delivery of the complexes. At step 170, the mito-transferred colonies are selected. In this study, rho(0) cells were selected using uridine-free media, e.g., from days 4-10 with the number of expanding colonies collected and counted on day 10.

Any of the above parameters may be varied to optimize reaction conditions, including but not limited to: the buffer to form cargo+PBAE complexes, concentrations of cargo and PBAE, pH, temperature, time of incubation of PBAE and cargo, centrifugation times and speeds, resuspension buffer for administration to recipient cells, and selection of transfected cells (e.g., concentration of uridine free media, length of time of selection, etc.). In some aspects, the amount of PBAE to cargo (PBAE:cargo) may be mixed at a 30 (30:1), at a 60 (60:1), or at a 90 (90:1) w/w ratio, in 25 mM sodium acetate buffer (pH=5.2), and after incubation, diluted into 150 mM PBS, at a pH 7.4.

In some aspects, a sodium acetate (NaOAc) buffer (25 mM) is used. The NaOAc buffer may be mixed with or diluted with osmotically balanced buffers such as PBS to be compatible with physiological processes. In some embodiments, NaOAc may be removed by pelleting the mito+PBAE complexes with centrifugation, pouring off the supernatant, and resuspending or diluting in a suitable isotonic buffer.

In some aspects, the pH, for example of cargo+PBAE formed in the first buffer, may range from about 5.0 to about 9.0, about 5 to about 8.5, about 5 to about 7.5, from about 5.1 to about 7.4, or any value in between. In some embodiments, the pH is about 5.2.

In some embodiments, cargo+PBAE complexes may be formed at any suitable temperature. Cargo+PBAE complexes (e.g., mito+PBAE complexes) may be formed on ice (~0° C.). The temperature may be varied, e.g., from about −20° C. to about 25° C. to optimize cargo+PBAE complex formation.

In some aspects, the incubation time of cargo+PBAE may range from about 30 s, about 1 min., about 2 min., about 3 min., about 4 min., about 5 min., about 10 minutes, about 15 minutes, about 20 minutes, about 30 minutes or more up to about 1 hour, about 2 hours, about 3 hours, or more, or any amount in between, for example, from about 30 s to about 3 hours, about 1 min to about 2 hours, about 5 minutes to about 1 hour or about 10 minutes to about 30 minutes.

The concentration of PBAE may be varied from about 0.1 mg/ml, about 1 mg/ml, about 2 mg/ml, about 3 mg/ml, about 4 mg/ml, about 5 mg/ml up to about 10 mg/ml, about 20 mg/ml, about 25 mg/ml, and about 50 mg/ml, based on total volume. In other aspects, the PBAE concentration is about 5 mg/ml.

Example mitochondrial transfection results are shown in FIG. 4. For this set of experiments, sodium acetate buffer at a pH of 5.2 was used to form complexes between mito+PBAE, and these complexes were transferred into 143 BTK rho(0) cells for selection in uridine free media.

A variety of buffers and concentrations were tested. To obtain colonies (indicating successful transfection without mechanical force), the concentration of PBAE was about 1-5 mg/ml. The yield was further improved by diluting NaOAc buffer (1:1 with PBS or 1:9 with PBS).

Advantages of the present techniques include delivery of isolated mitochondria (using PBAE) into cultured cell lines, wherein the delivered mitochondrial DNA is stably integrated into the cell. Additionally, the colony forming efficiency is similar to or higher than mechanical methods of transfection. Moreover, mitochondrial delivery with PBAE may be used in vivo, e.g., by injecting the PBAE complexed mitochondria, which may be resuspended or diluted in PBS, into the recipient patient. PBAE may also be used to deliver other large molecules, including but not limited to mitochondria, organelles, proteins, tumor antigens, exosomes, etc. to recipient cells. In contrast, mechanical methods are limited to in vitro use. In other aspects, the techniques provided herein may be used to transfect embryos with corrected mito+PBAE complexes to treat diseases. These techniques may be used to transfect diseased tissues with corrected mitochondria.

In some aspects, the mito+PBAE complexes, which may form nano- or micro-particles, may be lyophilized and stored for later use. The lyophilized complexes may be mixed with PBS or saline buffer prior to administration.

In some aspects, and further to the examples provided below, steps and parameters may be specifically designed and optimized for transfection into specific cells.

EXAMPLES

Example 1. Synthesis of PBAE Molecules

Techniques for polymer synthesis are known in the art. The experimental protocol provided in Mangravati et al. (supra) is as follows:

PBAEs were synthesized using a two-step reaction in a manner similar to Bhise et al. (supra). Base monomers B4, B5, or B6 (where "4," "5," and "6" represent the number of carbons of the variable alkyl chains within those monomers) were each polymerized by Michael Addition of one of the side chain monomers S3, S4, or S5 (where "3", "4," and "5," represent the number of carbons of the variable alkyl chains within those monomers) at suitable ratios for 24 h at 90° C. in the absence of solvent. Monomer acrylate-to-amine molar ratios used for synthesis range from 1.2:1 to 1.05:1.

For the second step of synthesis, the diacrylate-terminated base polymers were dissolved in anhydrous tetrahydrofuran (THF, Sigma) at 100 mg/mL and combined with 0.2 M amine containing small molecules as polymer end-capping groups. The reaction was conducted for 1 h at room temperature while shaking. Polymers were then purified to remove excess monomer via precipitation in diethyl ether. The ether was decanted to collect polymer, and the polymer was washed again with ether; the ether was decanted, and then the polymer was allowed to dry under vacuum for 48 h. The neat polymers were then dissolved in dimethyl sulfoxide (DMSO) at 100 mg/mL and were stored at −20° C. in small aliquots to limit freeze-thaw cycles. The molecular weight and polydispersities of the polymers may be determined by gel permeation chromatography (GPC; Waters, Milford, Mass.) in BHT-stabilized tetrahydrofuran with 5% DMSO and 1% piperidine. Number-averaged and weight-averaged molecular weights (Mn and Mw, respectively) are measured using polystyrene standards. Purity of the leading polymer, 1-(3-aminopropyl)-4-methylpiperazine end-modified (or end-capped) poly-(1,4-butanediol diacrylate-co-4-amino-1-butanol) (447), may be confirmed by 1H NMR spectra.

Example 2. Transfection of 143 BTK Rho(0) Cells

The polymer shown in FIG. 2, 1-(3-aminopropyl)-4-methylpiperazine end-capped poly-(1,4-butanediol diacrylate-co-4-amino-1-butanol) (referred to hereafter as "PBAE") was used to transfect cells according to the experimental protocol in FIGS. 3A and 3B. On day 0, mitochondria was isolated from DsRed HEK cells. Mitochondria was incubated with PBAE in sodium acetate buffer, pH 5.2 (or diluted in PBS) for about 5 min to form a mito+PBAE complex. The complexed mito+PBAE was spun down and re-suspended in PBS. The complex was delivered into 143BTK rho(0) cells using present techniques (TOP) or mechanical methods (PUNCH) as a comparison. Cells were harvested and re-plated 24 hrs after mito delivery, and mito-transferred colonies were selected with uridine-free media from days 4-10. On day 10, the number of expanding colonies was counted.

A more detailed mito+PBAE complex formation protocol which was performed is provided as follows:

Isolated mitochondria were divided into an appropriate number of 1.7 mL snap-top tubes based on the estimated amount of mitochondria and the desired number of experimental conditions. The tubes were spun down at 6000×g at 4° C. and the supernatant was removed, and kept briefly on ice.

PBAE complexing solutions were prepared by first measuring the appropriate volume of 100 mg/mL PBAE in DMSO into a 1.7 mL tube, and then adding the desired buffer and mixing vigorously for ~10 s by pipette. For mixed NaOAc and PBS buffers, the PBAE was first dissolved into 25 mM NaOAC (pH 5.2), and then this solution was diluted with PBS.

For each tube containing mitochondria, 50 μL of the PBAE solution was added and mixed by pipette to resuspend the pellet.

Mitochondria were incubated in the PBAE solution for 5 minutes on ice, then spun down at 6000×g at 4° C., and then the supernatant was removed. The pellet was resuspended in PBS, typically about 100 μL.

FIG. 4 shows experimental results of the process of FIGS. 3A-3B. All of the mito samples were prepared together as a single batch. This was done using the "Qproteome Mitochondria Isolation Kit" from Qiagen. As shown by these results, PBAE or mechanical force was required for transfection. Concentrations of PBAE ranged from 1-5 mg/ml, and resuspension in an isotonic buffer greatly improved colony yield.

Unexpectedly, the techniques provided herein led to the successful transfection of large cargo (e.g., mitochondria) into cells without mechanical force. Surprisingly, even without optimization of individual components of this process, the results were substantially improved over mechanical methods.

Example 3. Transfection of Cells with Virus+PBAE Complex

Figure 5A:
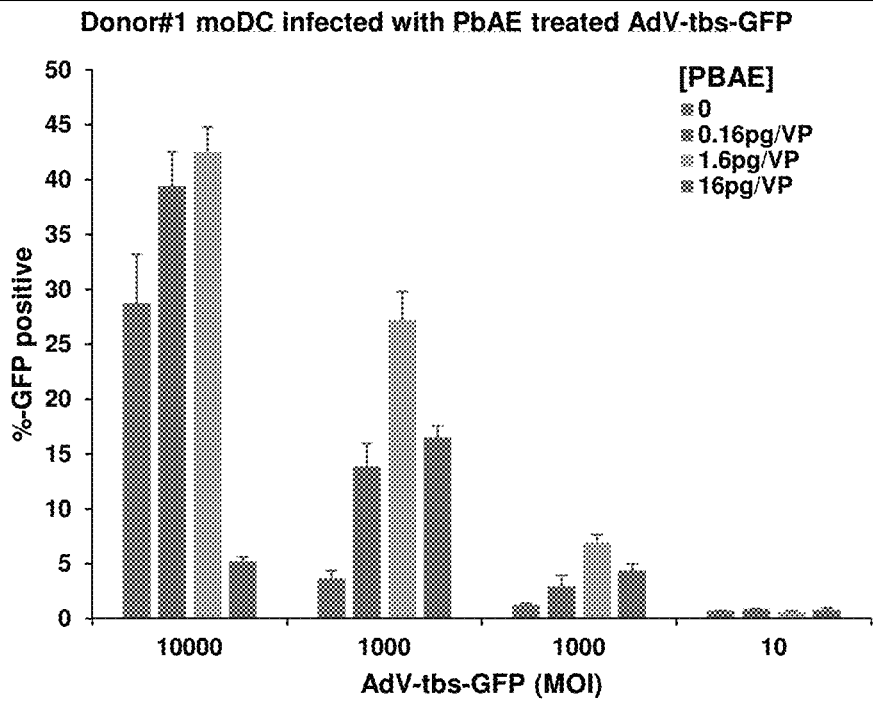
FIGS. 5A-5C shows experimental results for infection of monocyte-derived dendritic cells (MoDCs) with adenovirus (AdV) using PBAE according to some embodiments provided herein.
Figure 5B:
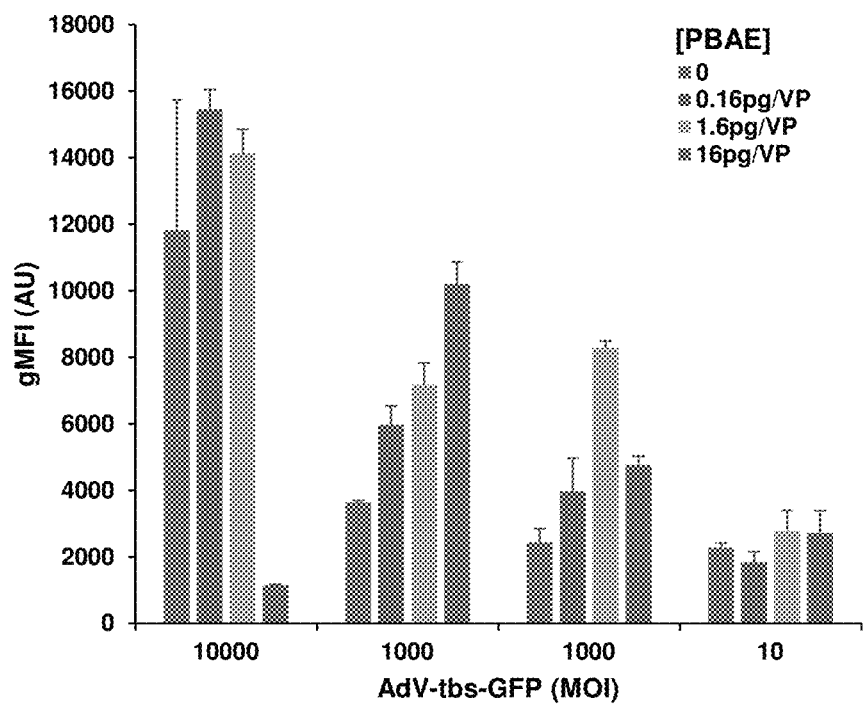
Figure 5C:
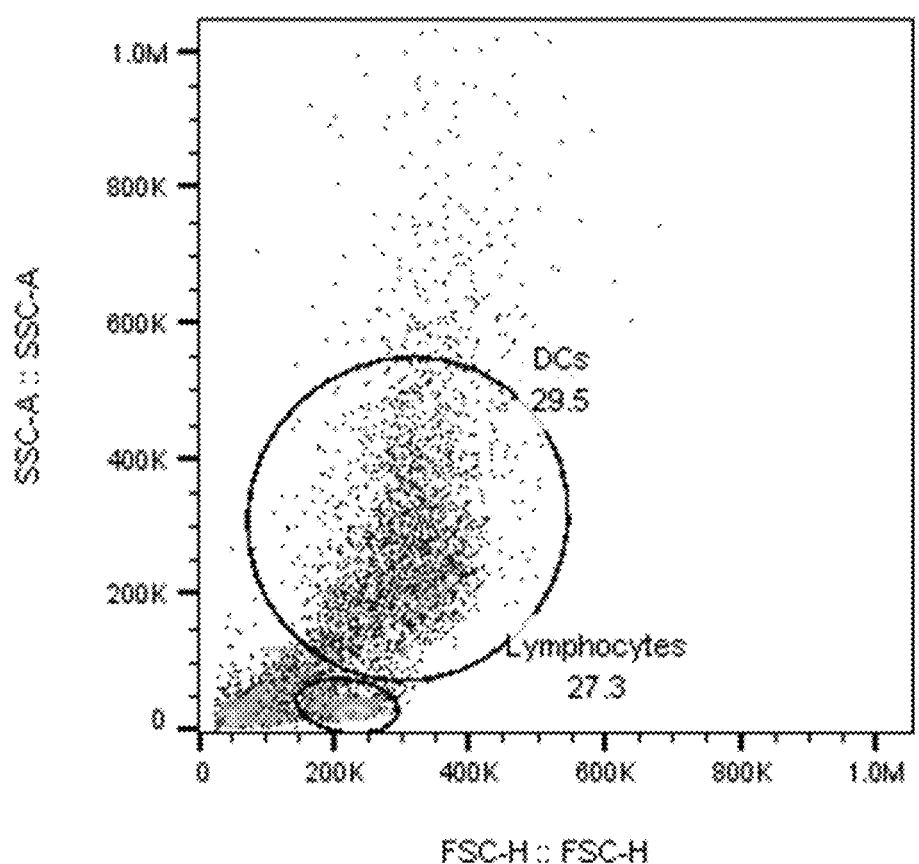
Figure 6A:
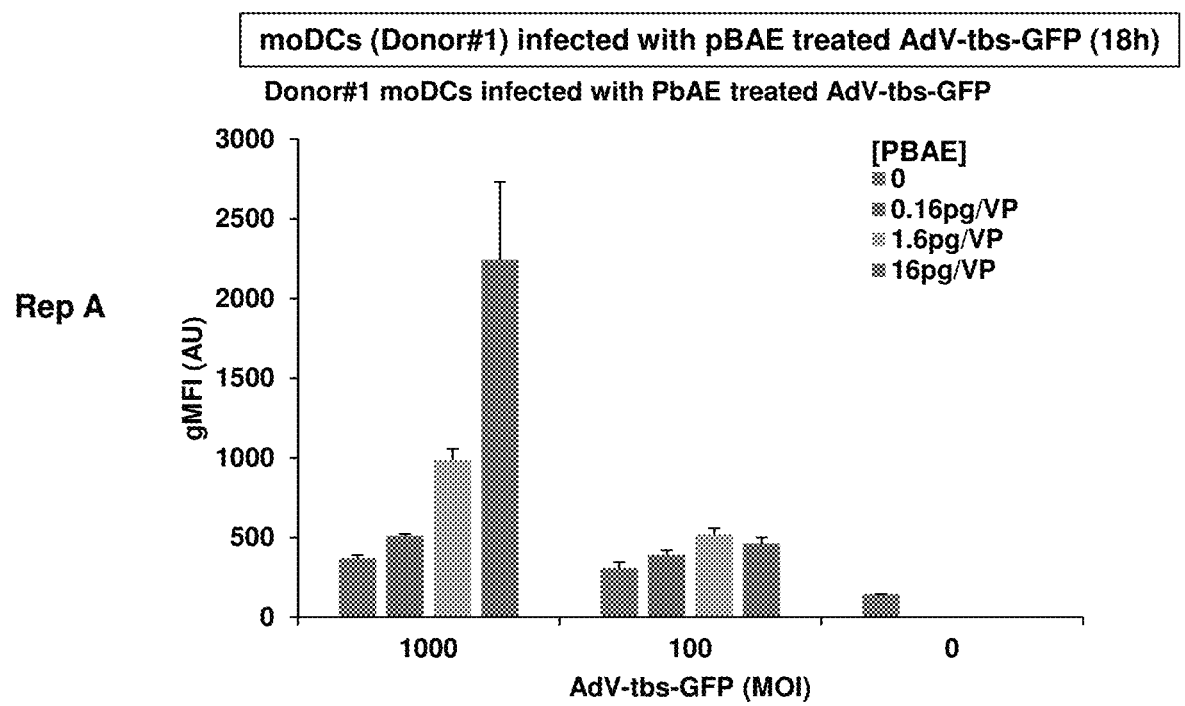
FIGS. 6A-6G shows experimental results for infection of monocyte-derived dendritic cells (MoDCs) with AdV using PBAE according to some embodiments provided herein.
Figure 6B:
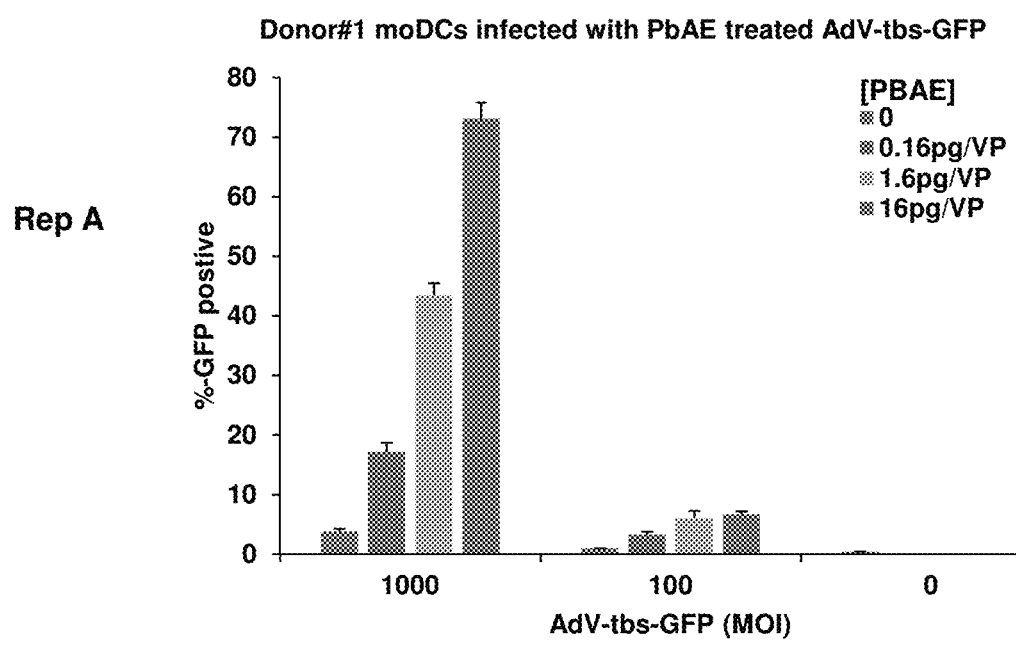
Figure 6C:
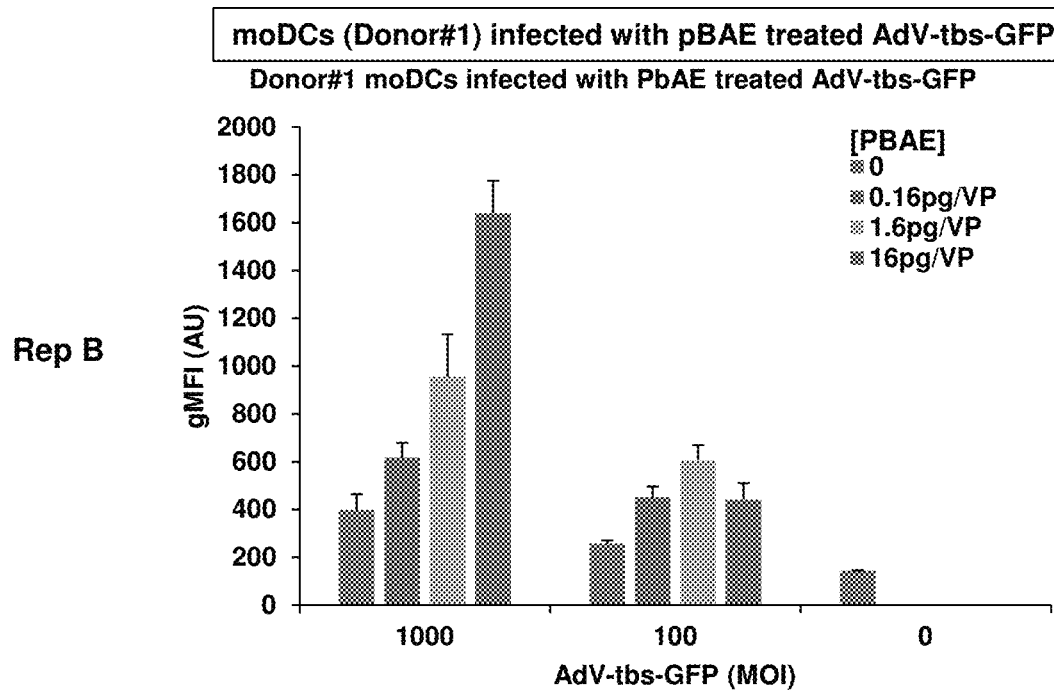
Figure 6D:
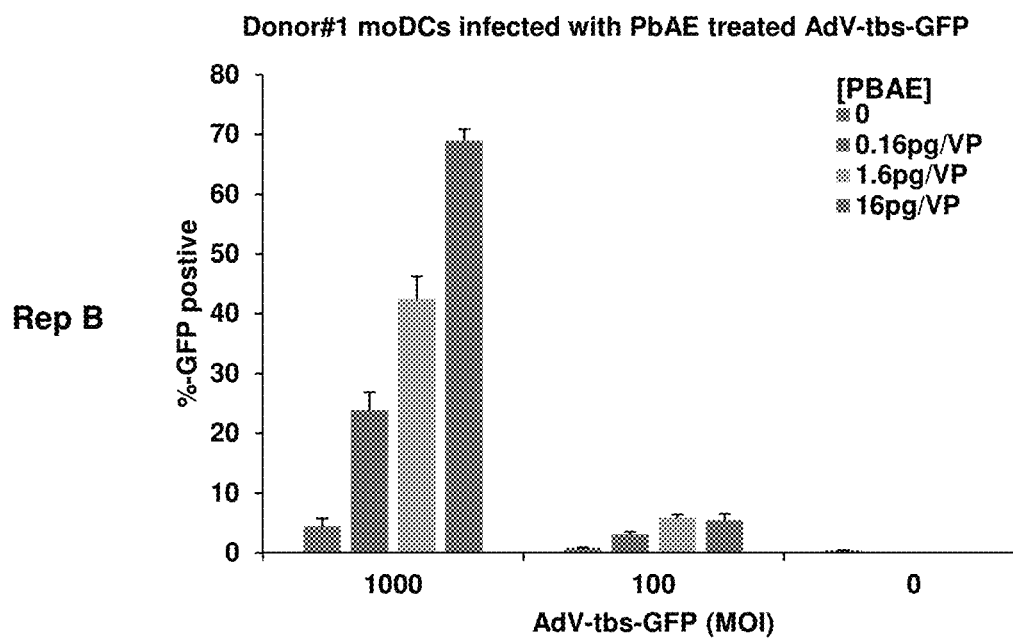
Figure 6E:
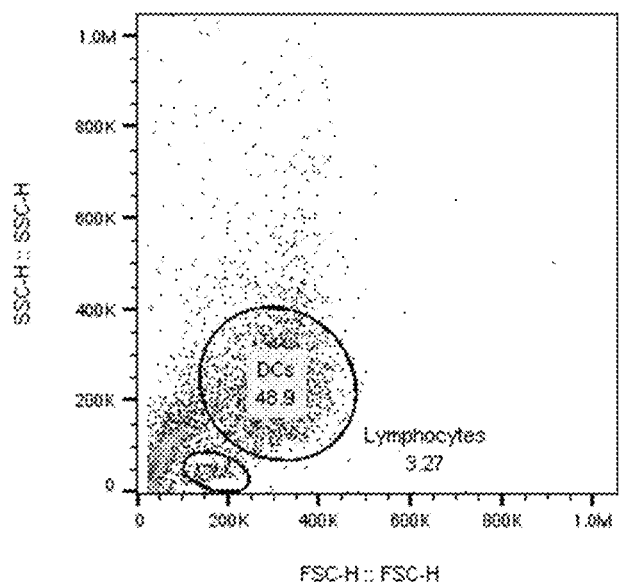
Figure 6F:
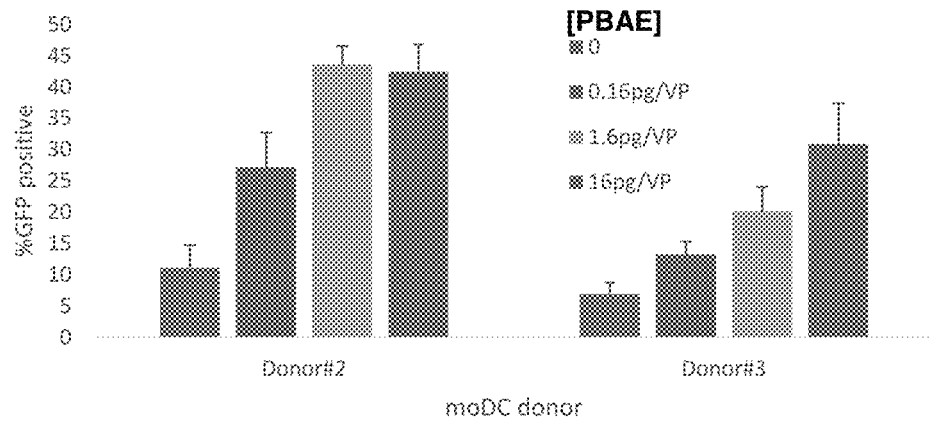
Figure 6G:
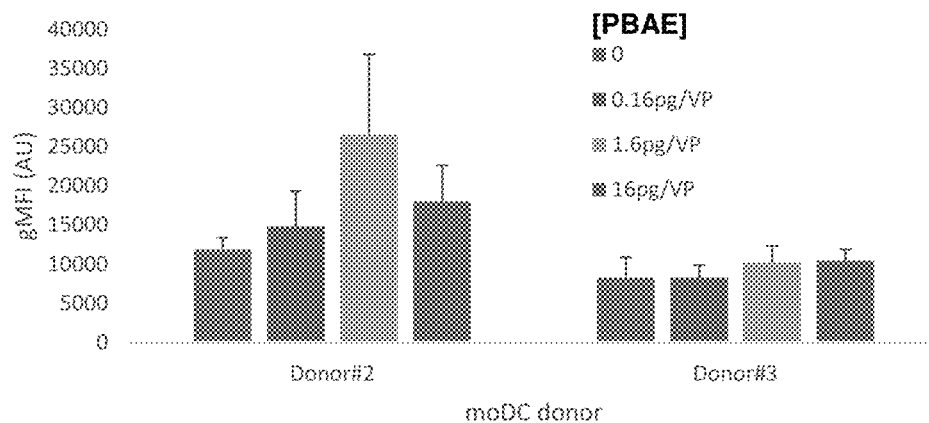
Figure 7A:
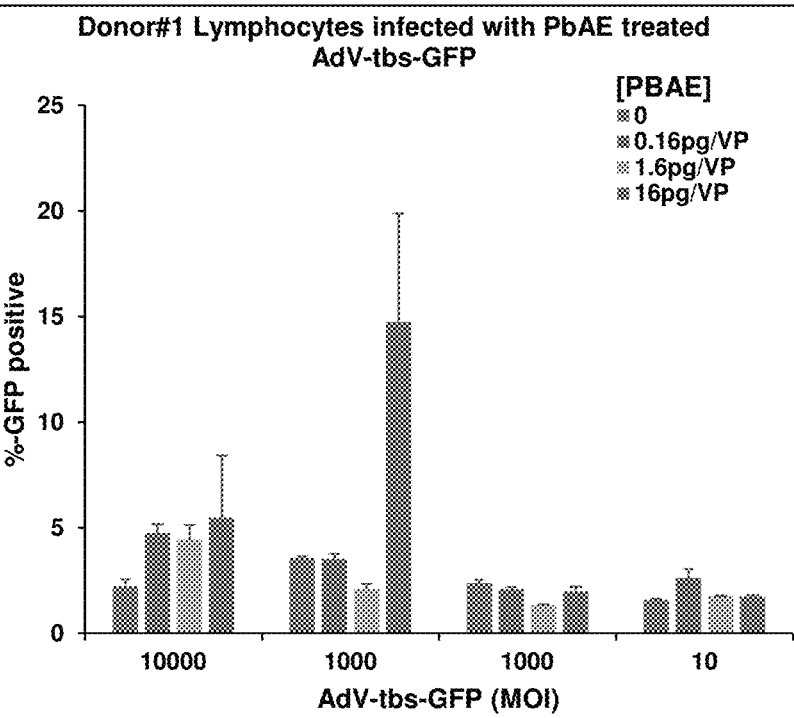
FIGS. 7A-7E shows experimental results for infection of lymphocytes with AdV using PBAE according to some embodiments provided herein.
Figure 7B:
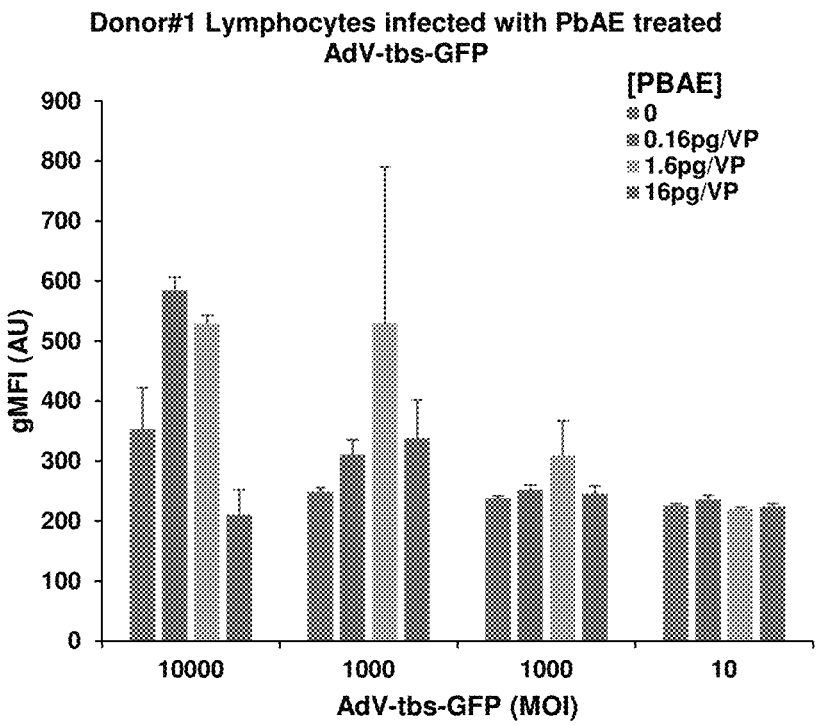
Figure 7C:
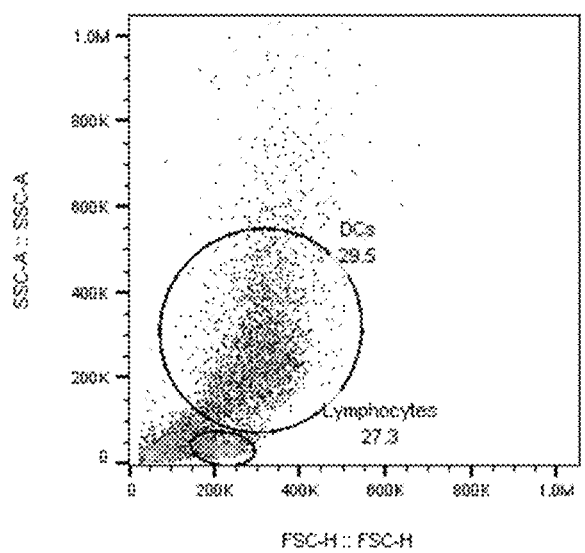
Figure 7D:
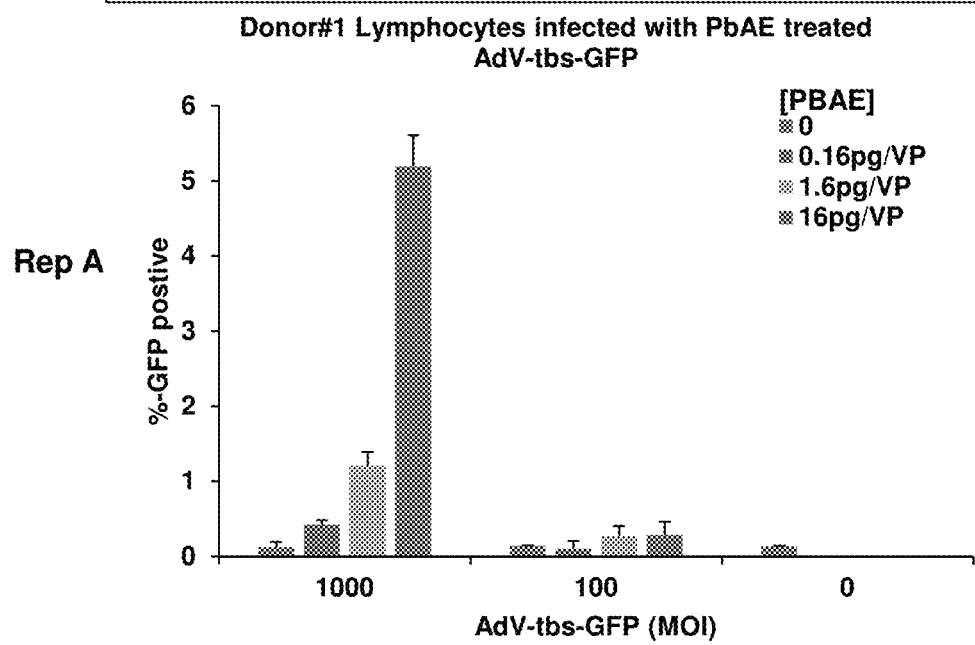
Figure 7E:
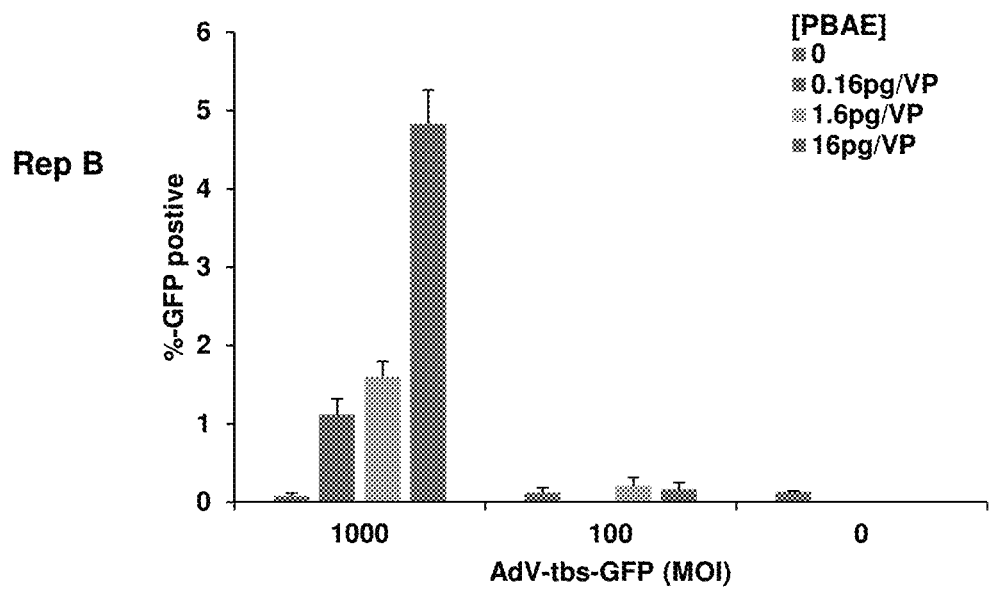

Virus+PBAE complexes were formed using adenovirus 5 (AdV) and PBAE in a similar protocol as provided in Example 2 for formation of the mito+PBAE complexes except that they were incubated for 10 minutes instead of 5 minutes, and the virus+PBAE complexes were added directly to the cell culture after their formation, with no washing step. The cells transfected (or infected) with the virus+PBAE complexes were monocyte-derived dendritic cells (MoDCs) and lymphocytes. FIGS. 5A-5C shows experimental results for infection of monocyte-derived dendritic cells (MoDCs) with adenovirus (AdV) using PBAE. These results were obtained by coating PBAE, at 3 different concentrations, onto AdV that encoded for green fluorescent protein (GFP). These coated AdV, as well as uncoated AdV, were then allowed to infect cultures of MoDCs at four different multiplicities of infection (MOIs). The rate and intensity of infection were then measured by flow cytometry as a percentage of GFP positive cells and a geometric mean fluorescence intensity (gMFI) of those cells. The results indicate an enhancement of infectivity for AdV coated with PBAE.

FIGS. 6A-6G shows experimental results for infection of monocyte-derived dendritic cells (MoDCs) with AdV using PBAE. These results were obtained from independent replications of the experiment from which the MoDC results shown in FIGS. 5A-5C were obtained. These results show reproducibility of the enhancement of infectivity observed in PBAE coated AdV toward MoDCs across multiple independent experiments and MoDCs derived from three separate donors.

FIGS. 7A-7E shows experimental results for infection of lymphocytes with AdV using PBAE. These results were obtained from the same experiments from which the moDC results shown in FIGS. 5A-5C and FIGS. 6A-6G were obtained by morphologically gating during flow cytometry analysis for residual lymphocytes found in the MoDC cultures. These results indicate that the preferential infectivity of AdV toward dendritic cells relative to lymphocytes is by and large preserved in PBAE coated AdV.

In FIGS. 5A-7E, the legend values from top to bottom correspond from left to right, respectively, of the bar data on the x-axis for each value on the x-axis.

Example 4. Transfection of Target Cells

In some embodiments, a targeting molecule (e.g., a binding domain of an antibody, protein, etc.) may be attached to the cargo to target the cargo to an appropriate target. For example, to target the cargo to T cells, an anti-CD3/anti-CD28 binding domain may be attached to the cargo or surface of the cargo+PBAE complex. Once reaching its target destination, uptake of the nano- or micro-complex may occur, according to the techniques provided herein.

In some embodiments, the numbers expressing quantities of ingredients, properties such as concentration, reaction conditions, and so forth, used to describe and claim certain embodiments are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments are approximations, the numerical values set forth in the specific examples are reported as precisely as practicable. The numerical values presented in some embodiments may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

It should also be apparent to those skilled in the art that many more modifications besides those already described herein are possible without departing from the concepts provided herein. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of transfecting cells with a cargo, comprising forming a complex of the cargo with a poly(beta-amino ester) (PBAE) molecule, and contacting the complex with the cells, wherein the cargo is selected from the group consisting of mitochondria, a protein, an exosome, an organelle, a tumor antigen, a bacteria, a yeast, and a virus, wherein the bacteria has a dimension of greater than or equal to 2.5 µm.

2. The method of claim 1, wherein the PBAE molecule is formed by reacting a primary amine with a di(acrylate ester).

3. The method of claim 1, wherein the primary amine corresponds to the formula, $NH_2R'$, wherein $R'$ is a $C_1$-$C_{20}$-alkyl or $—R^aR^b$, and wherein $R^a$ is a $C_1$-$C_{20}$-alkylene and $R^b$ is a hydroxyl group.

4. The method of claim 2, wherein the primary amine is selected from the group consisting of 3-amino-1-propanol, 4-amino-1-butanol, 5-amino-1-pentanol, 2-(4-hydroxyphenyl)ethylamine, and 4-amino-N,N-dimethylbutanamide.

5. The method of claim 2, wherein the di(acrylate ester) corresponds to the formula:

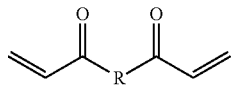

wherein R is —O-P-O—, wherein O is oxygen and P is a $C_1$-$C_{20}$-alkylene.

6. The method of claim 2, wherein the di(acrylate ester) is selected from the group consisting of 1,4-butanediol diacrylate; 1,5-pentanediol diacrylate; 1,3-propanediol diacrylate; 1,6-hexanediol diacrylate; 1,3-butanediol diacrylate; and 1,4-cyclohexanedimethanol diacrylate.

7. The method of claim 1, wherein the PBAE molecule is selected from the group consisting of poly(1,4-butanediol diacrylate-co-4-amino-1-butanol) poly(1,5-pentanediol diacrylate-co-4-amino-1-butanol); poly(1,4-butanediol diacrylate-co-5-amino-1-pentanol); and poly(1,5-pentanediol diacrylate-co-5-amino-1-pentanol).

8. The method of claim 1, wherein the PBAE molecule is an end-capped PBAE molecule formed by reacting the PBAE molecule with a capping amine.

9. The method of claim 8, wherein the capping amine corresponds to the formula, $NH_2$—R", wherein R" is a $C_1$-$C_{20}$-alkyl, a $C_1$-$C_{20}$ nitrogen-containing alkyl, or $—R^cR^d$, wherein $R^c$ is a $C_1$-$C_{20}$-alkylene, or a $C_1$-$C_{20}$ nitrogen-containing alkylene and $R^b$ is a hydroxyl group or an amino group.

10. The method of claim 8, wherein the capping amine is selected from the group consisting of 1-(3-aminopropyl)-4-methylpiperazine; pentane-1,3-diamine; 2-((3-aminopropyl)amino)ethan-1-ol; and 1,3-diaminopropane; or the capping amine is $[NH_2(CH_2CH_2O)_mCH_2CH_2NH_2]$, wherein m is an integer from 3 to 12.

11. The method of claim 1, wherein the PBAE molecule is 1-(3-aminopropyl)-4-methylpiperazine end-capped poly-(1,4-butanediol diacrylate-co-4-amino -1-butanol).

12. The method of claim 1, wherein the concentration of the PBAE molecule is 1.0 to 20.0 mg/ml.

13. The method of claim 1, wherein the cargo is mitochondria.

14. The method of claim 1, wherein the cargo is selected from the group consisting of mitochondria, a protein, an exosome, an organelle, a tumor antigen, a yeast, and a virus.

15. The method of claim 1, wherein the mitochondria, the protein, the exosome, the organelle, the tumor antigen, the yeast and the virus each have at least one dimension of at least about 0.1 µm.

16. The method of claim 1, wherein the mass ratio of the PBAE molecule to cargo is about 30, about 60 or about 90 polymer-to-cargo (w/w).

17. The method of claim 1, wherein the complex of PBAE and cargo is formed in a first buffer having a pH of about 5.0 to about 9.0.

18. The method of claim 17, wherein the first buffer is sodium acetate.

19. The method of claim 1, wherein the cells are selected from the group consisting of NK cells, EC-7 cells, T cells, embryonic cells, and cells with defective mitochondria.

20. The method of claim 1, wherein the number of colonies per $10^5$ cells transfected with the cargo is at least 50.

21. The method of claim 1, further comprising mixing the complex with an isotonic buffer, prior to contacting the complex with the cells.

22. The method of claim 1, wherein mechanical force is not used.

23. A method of in vivo transfection, comprising:
forming a complex of a cargo with a PBAE molecule; and administering the complex mixed with an isotonic buffer to a patient to treat a disease or disorder, wherein the cargo is selected from the group consisting of mitochondria, a protein, an exosome, an organelle, a tumor antigen, a bacteria, a yeast, and a virus, wherein the bacteria has a dimension of greater than or equal to 2.5 µm.

24. The method of claim 23, wherein the PBAE molecule is formed by reacting a primary amine with a di(acrylate ester).

25. The method of claim 24, wherein the primary amine corresponds to the formula, $NH_2R'$, wherein $R'$ is a $C_1$-$C_{20}$-alkyl or $—R^aR^b$, and wherein $R^a$ is a $C_1$-$C_{20}$-alkylene and $R^b$ is a hydroxyl group.

26. The method of claim 24, wherein the primary amine is selected from the group consisting of 3-amino-1-propanol, 4-amino-1-butanol, 5-amino-1-pentanol, 2-(4-hydroxyphenyl)ethylamine, and 4-amino-N,N-dimethylbutanamide.

27. The method of claim 24, wherein the di(acrylate ester) corresponds to the formula:

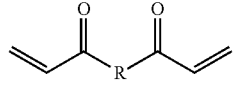

wherein R is —O-P-O—, wherein O is oxygen and P is a $C_1$-$C_{20}$-alkylene.

28. The method of claim 24, wherein the di(acrylate ester) is selected from the group consisting of 1,4-butanediol diacrylate; 1,5-pentanediol diacrylate; 1,3-propanediol diacrylate; 1,6-hexanediol diacrylate; 1,3-butanediol diacrylate; and 1,4-cyclohexanedimethanol diacrylate.

29. The method of claim 23, wherein the PBAE is selected from the group consisting of poly(1,4-butanediol diacrylate-co-4-amino-1-butanol) poly(1,5-pentanediol diacrylate-co- 4-amino-1-butanol); poly(1,4-butanediol diacrylate-co-5-amino-1-pentanol); and poly(1,5-pentanediol diacrylate-co-5-amino-1-pentanol).

30. The method of claim 23, wherein the PBAE molecule is an end-capped PBAE molecule formed by reacting the PBAE molecule with a capping amine.

31. The method of claim 30, wherein the capping amine corresponds to the formula, $NH_2$—R'', wherein R'' is a $C_1$-$C_{20}$-alkyl, a $C_1$-$C_{20}$ nitrogen-containing alkyl, or —$R^cR^d$, wherein $R^c$ is a $C_1$-$C_{20}$-alkylene, or a $C_1$-$C_{20}$ nitrogen-containing alkylene and $R^b$ is a hydroxyl group or an amino group.

32. The method of claim 30, wherein the capping amine is selected from the group consisting of 1-(3-aminopropyl)-4-methylpiperazine; pentane-1,3-diamine; 2-((3-aminopropyl)amino)ethan-1-ol; and 1,3-diaminopropane; or the capping amine is [$NH_2(CH_2CH_2O)_mCH_2CH_2NH_2$], wherein m is an integer from 3 to 12.

33. The method of claim 23, wherein the PBAE molecule is 1-(3-aminopropyl)-4-methylpiperazine end-capped poly-(1,4-butanediol diacrylate-co-4-amino-1-butanol).

34. The method of claim 23, wherein the cargo is selected from the group consisting of a mitochondria, a protein, an exosome, an organelle, a tumor antigen, a yeast, and a virus.

35. The method of claim 23, wherein the mitochondria, the protein, the exosome, the organelle, the tumor antigen, the yeast and the virus each have at least one dimension of at least about 0.1 μm.

36. The method of claim 23, wherein the mass ratio of the PBAE molecule to cargo is about 30, about 60 or about 90 polymer-to-cargo (w/w).

37. The method of claim 23, wherein the disease is selected from the group consisting of a mitochondrial disorder, cardiac dysfunction, heart failure, autism, diabetes mellitus, and deafness.

38. The method of claim 23, wherein mechanical force is not used.

39. The method of claim 1, wherein the mitochondria, the protein, the exosome, the organelle, the tumor antigen, the yeast, and the virus each have at least one dimension ranging from about 0.1 μm to about 10 μm.

40. The method claim 23, wherein the mitochondria, the protein, the exosome, the organelle, the tumor antigen, the yeast, and the virus each have at least one dimension ranging from about 0.1 μm to about 10 μm.

41. The method of claim 23, wherein the cargo is mitochondria.

42. A method of transfecting cells with a cargo, comprising forming a complex of the cargo with a poly(beta-amino ester) (PBAE) molecule, and contacting the complex with the cells, wherein the cargo is mitochondria.

43. A method of in vivo transfection, comprising:
forming a complex of a cargo with a poly(beta-amino ester) (PBAE) molecule; and
administering the complex mixed with an isotonic buffer to a patient to treat a disease or disorder, wherein the cargo is mitochondria.

\* \* \* \* \*